(12) United States Patent
Chang et al.

(10) Patent No.: US 9,107,654 B2
(45) Date of Patent: Aug. 18, 2015

(54) ATTACHMENT DEVICE FOR TISSUE APPROXIMATION AND RETRACTION

(71) Applicant: Cook Medical Technologies LLC, Bloomington, IN (US)

(72) Inventors: Kenneth J. Chang, Cerritos, CA (US); Kevin Chmura, Lewisville, NC (US); Richard W. Ducharme, Alexandria, PA (US); Tyler E. McLawhorn, Winston-Salem, NC (US)

(73) Assignee: Cook Medical Technologies LLC, Bloomington (IN)

( * ) Notice: Subject to any disclaimer, the term of this patent is extended or adjusted under 35 U.S.C. 154(b) by 256 days.

(21) Appl. No.: 13/733,420

(22) Filed: Jan. 3, 2013

(65) Prior Publication Data

US 2013/0178899 A1    Jul. 11, 2013

Related U.S. Application Data

(60) Provisional application No. 61/583,409, filed on Jan. 5, 2012.

(51) Int. Cl.
*A61B 17/04* (2006.01)
*A61B 17/00* (2006.01)

(52) U.S. Cl.
CPC ......... *A61B 17/0401* (2013.01); *A61B 17/0057* (2013.01); *A61B 17/0483* (2013.01); *A61B 2017/00336* (2013.01); *A61B 2017/00477* (2013.01); *A61B 2017/00663* (2013.01);
(Continued)

(58) Field of Classification Search
CPC ........... A61B 17/0401; A61B 17/0057; A61B 2017/00663; A61B 2017/0464; A61B 2017/0441; A61B 2017/0443; A61B 2017/0409

USPC .......... 606/139, 144, 148, 150, 232
See application file for complete search history.

(56) References Cited

U.S. PATENT DOCUMENTS 4,632,100 A * 12/1986 Somers et al. ............... 606/232
5,217,486 A * 6/1993 Rice et al. .................... 606/232
(Continued)

FOREIGN PATENT DOCUMENTS

EP        1 759 663 A2    3/2007
WO   WO 2007/076018 A2    7/2007
WO   WO 2010/128502 A1   11/2010

OTHER PUBLICATIONS

International Search Report mailed Apr. 25, 2013 for International Application No. PCT/US2013/020258.

(Continued)

*Primary Examiner* — Jonathan W Miles
(74) *Attorney, Agent, or Firm* — Brinks Gilson & Lione (57) ABSTRACT

An attachment system for tissue apposition or manipulation and a method of attaching a suture to a tissue for apposition or manipulation of the tissue are provided. The system includes an attachment device including a body having a proximal portion and a distal portion. The attachment device further includes a tissue attachment portion operably connected to the distal portion wherein the tissue attachment portion has a shape that is maintained throughout a tissue apposition procedure. The attachment device also includes a suture operably connected to the body and having an unconnected proximal end and a retaining structure at the proximal portion of the body. The retaining structure configured to releasably mate with a complementary retaining structure on a stylet.

7 Claims, 7 Drawing Sheets

(52) U.S. Cl.
CPC . *A61B2017/0409* (2013.01); *A61B 2017/0441* (2013.01); *A61B 2017/0464* (2013.01)

(56) References Cited

U.S. PATENT DOCUMENTS

| | | | |
|---|---|---|---|
| 5,246,014 A | | 9/1993 | Williams et al. |
| 5,304,195 A | * | 4/1994 | Twyford et al. ............... 606/191 |
| 5,324,308 A | * | 6/1994 | Pierce ........................... 606/232 |
| 5,330,503 A | | 7/1994 | Yoon |
| 5,443,482 A | * | 8/1995 | Stone et al. .................... 606/232 |
| 5,458,608 A | * | 10/1995 | Wortrich ........................ 606/139 |
| 5,573,548 A | * | 11/1996 | Nazre et al. .................... 606/232 |
| 5,582,616 A | | 12/1996 | Bolduc et al. |
| 5,584,835 A | * | 12/1996 | Greenfield .................... 606/232 |
| 5,591,207 A | * | 1/1997 | Coleman ....................... 606/232 |
| 5,607,432 A | * | 3/1997 | Fucci ............................ 606/104 |
| 5,626,613 A | | 5/1997 | Schmieding |
| 5,626,614 A | | 5/1997 | Hart |
| 5,662,683 A | | 9/1997 | Kay |
| 5,665,111 A | * | 9/1997 | Ray et al. ...................... 606/232 |
| 5,728,116 A | | 3/1998 | Rosenman |
| 5,810,851 A | | 9/1998 | Yoon |
| 5,810,882 A | | 9/1998 | Bolduc et al. |
| 5,843,127 A | * | 12/1998 | Li ................................. 606/232 |
| 5,988,171 A | | 11/1999 | Sohn et al. |
| 6,045,573 A | * | 4/2000 | Wenstrom et al. ............ 606/232 |
| 6,171,320 B1 | | 1/2001 | Monassevitch |
| 6,884,248 B2 | | 4/2005 | Bolduc et al. |
| 6,960,217 B2 | | 11/2005 | Bolduc et al. |
| 6,986,776 B2 | | 1/2006 | Craig |
| 7,306,614 B2 | | 12/2007 | Weller |
| 7,431,725 B2 | | 10/2008 | Stack et al. |
| 2002/0120292 A1 | * | 8/2002 | Morgan ........................ 606/232 |
| 2003/0014127 A1 | | 1/2003 | Talja et al. |
| 2003/0130669 A1 | * | 7/2003 | Damarati ...................... 606/151 |
| 2005/0090861 A1 | | 4/2005 | Porter |
| 2006/0135971 A1 | | 6/2006 | Swanstrom et al. |
| 2007/0198050 A1 | * | 8/2007 | Ravenscroft et al. .......... 606/200 |
| 2007/0282355 A1 | | 12/2007 | Brown et al. |
| 2008/0045976 A1 | | 2/2008 | Gibbons, Jr. et al. |
| 2008/0045982 A1 | | 2/2008 | To et al. |
| 2008/0300629 A1 | | 12/2008 | Surti |
| 2009/0069847 A1 | | 3/2009 | Hashiba et al. |
| 2009/0240326 A1 | * | 9/2009 | Wilson et al. ................. 623/2.11 |
| 2009/0275971 A1 | | 11/2009 | Kelleher et al. |
| 2010/0145385 A1 | | 6/2010 | Surti et al. |

OTHER PUBLICATIONS

Written Opinion of the International Searching Authority mailed Apr. 25, 2013 for International Application No. PCT/US2013/020258.

* cited by examiner

ATTACHMENT DEVICE FOR TISSUE APPROXIMATION AND RETRACTION

RELATED APPLICATIONS

This application claims the benefit of U.S. Provisional Application No. 61/583,409, filed Jan. 5, 2012, which is incorporated by reference herein in its entirety.

BACKGROUND

Tissue perforations in the walls of internal organs and vessels may occur naturally may be formed intentionally or unintentionally. Numerous medical devices and methods have been developed to close the perforations and to allow the tissue to heal. In some procedures, it is desirable to retract tissue for further manipulation. For example, a fold may be created in the stomach that results in a gastric reduction by first placing an anchor through the stomach wall and tensioning the anchor so that the stomach wall invaginates. The gastric fold created may than be held in place with another anchor.

Devices currently used to close perforations and to hold tissues in position include clips, staples, anchors, sutures, adhesives and the like. The devices may be deployed using minimally invasive techniques, for example using endoscopic or laproscopic systems. For many tissue perforations, accessing the site and approximating the tissue to close the perforation requires complex and time consuming procedures. In some situations, the perforation may be larger than can be treated with a clip to hold the tissue together. For some perforations, the placement of the medical device at the proper site may be difficult. The delivery may be difficult due to engagement of the device within the delivery system, for example the device may be prematurely deployed or the placement may not allow proper apposition of the perforated tissue for healing. Some devices may be long enough to extend through the tissue, but uncontrolled insertion may lead to inadvertent puncturing of tissues due to the device extending too far. Some medical devices may not allow for repositioning of the device at the perforation site when the initial placement is not correct.

What is needed in the art is a medical device for repairing tissue perforations and for tensioning or holding tissues that is readily deployable at the tissue site, with controlled insertion and being repositionable to provide for proper tissue apposition. The medical device should also provide for apposition of large tissue perforations.

BRIEF SUMMARY

Accordingly, it is an object of the present invention to provide a device and a method having features that resolve or improve on the above-described drawbacks.

In one aspect, an attachment system for tissue apposition or manipulation is provided. The system includes an attachment device including a body having a proximal portion and a distal portion. The attachment device further includes a tissue attachment portion operably connected to the distal portion wherein the tissue attachment portion has a shape that is maintained throughout a tissue apposition procedure. The attachment device also includes a suture operably connected to the body and having an unconnected proximal end and a retaining structure at the proximal portion of the body. The retaining structure configured to releasably mate with a complementary retaining structure on a stylet.

In another aspect, a method of attaching a suture to a tissue for apposition or manipulation of the tissue is provided. The method includes forming a releasable connection between a stylet having a retaining portion and an attachment device having a complementary retaining portion and positioning an inner catheter over the connection to hold the stylet and the attachment device together at the retaining portions. The method further includes positioning a first tissue attachment portion of the attachment device at a first tissue site, rotating the stylet in an insertion direction to insert a distal tip of the tissue attachment portion into a tissue, the tissue attachment portion retaining its shape throughout the insertion and proximally withdrawing the inner catheter proximal to the connection to release the stylet from the attachment device and withdrawing the stylet and the attachment device remains with at least a portion of the attachment device positioned in the tissue.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the expandable biopsy device to a patient. Hence the term "distal" means the portion of the attachment device that is farthest from the physician and the term "proximal" means the portion of the attachment device that is nearest to the physician.

Figure 1A:
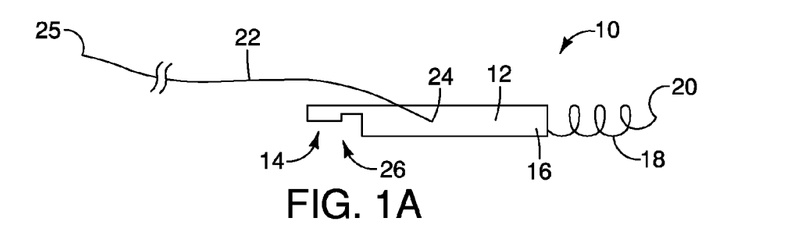
FIG. 1A is a side view of an embodiment of an attachment device in accordance with the present invention.
Figure 1B:
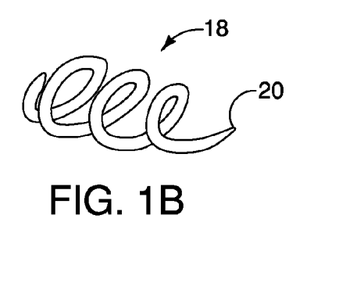
FIGS. 1B and 1C are partial views of embodiments of tissue attachment portions.
Figure 1C:
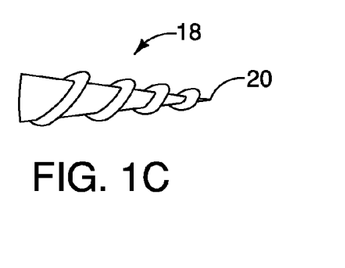

FIG. 1A illustrates an embodiment of an attachment device 10 in accordance with the present invention. The attachment device 10 includes a body 12 having a proximal portion 14 and a distal portion 16. A tissue attachment portion 18 is operably connected to the distal portion 16 of the body 12. In some embodiments, the tissue attachment portion 18 is a helical member having a sharp distal end 20 for piercing a patient's tissue. In some embodiments, the tissue attachment portion 18 may be a flattened spiral as shown in FIG. 1B or a threaded screw as shown in FIG. 10 to help hold the attachment device 18 in the tissue. Other configurations for the tissue attachment portion 18 are also possible. The tissue attachment portion 18 may be formed from a biocompatible material such as a metal or plastic and is configured to be rigid and to retain its shape from delivery through implantation into the patient's tissue. In some embodiments, the tissue attachment portion 18 is configured to be rotated about 4-5 rotations of the device 10 to insert into the tissue and may be removable from the tissue by the same number of rotations. In some embodiments, the tissue attachment portion 18 may be about 0.5 cm to about 2 cm in length, and in some embodiments, about 1 cm in length. In some embodiments, the attachment portion 18 may be formed from a wire having about a 0.01-0.04 inch O.D. and in some embodiments a wire having about a 0.02 inch O.D.

Figure 2:
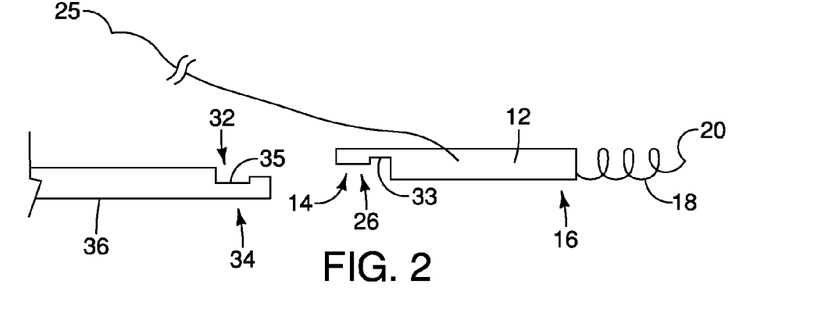
FIG. 2 is a side view of an embodiment of an attachment device and a stylet.
Figure 4:
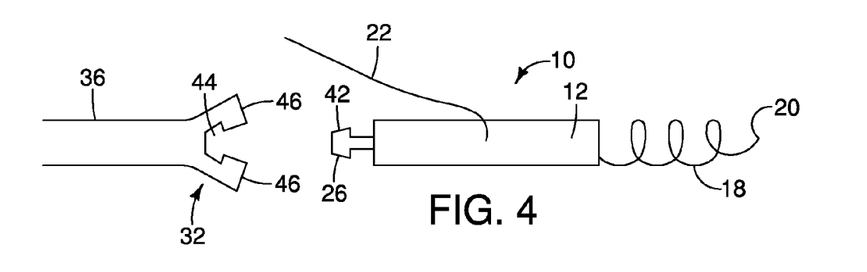
FIG. 4 is a side view of an embodiment of an attachment device and a stylet.

The attachment device 10 further includes a suture 22 having a distal portion 24 operably connected to the body 12 and a free end 25. The proximal portion 14 of the body 12 includes a first retainer 26. The first retainer 26 is configured to mate with a second retainer 32 provided on a distal portion 34 of a stylet 36 as shown in FIG. 2. The first retainer 26 and second retainer 32 have complimentary shapes that mate together to hold the attachment device 10 to the stylet 36 as described in more detail below. In the embodiment shown in FIG. 2, the first retainer 26 and the second retainer 32 have a half cylinder shape, each with a flattened portion 33, 35 that mate together. The first retainer 26 and the second retainer 32 may have any complimentary shape. See for example another shape shown in FIG. 4 where the first retainer 26 is a protrusion 42 that mates with the second retainer 32 that includes a recess 44. The recess 44 includes a pair of expandable arms 46 that enclose the protrusion 42 to hold the attachment device 10 to the stylet 36.

Figure 3:
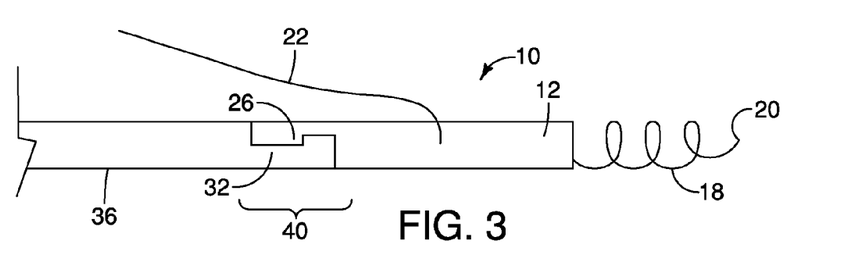
FIG. 3 is a side view of the attachment device and the stylet shown in FIG. 2 in a connected position.

As shown in FIG. 3, the attachment device 10 and the stylet 36 are mated together with the complimentary retainers 26, 32 joined. As shown in the embodiment of FIG. 3, when the complimentary retainers 26, 32 are joined, outer diameters of the stylet 36, a connection region 40 and attachment device 10 are substantially the same. The embodiment shown in FIG. 4 may also be joined so that when the complimentary retainers 26, 32 are joined, the arms 46 of the second retainer 32 fold in around the protrusion 42 of the first retainer so that the outer diameters of the stylet 36, the connection region 40 and attachment device 10 are substantially the same.

Figure 5:
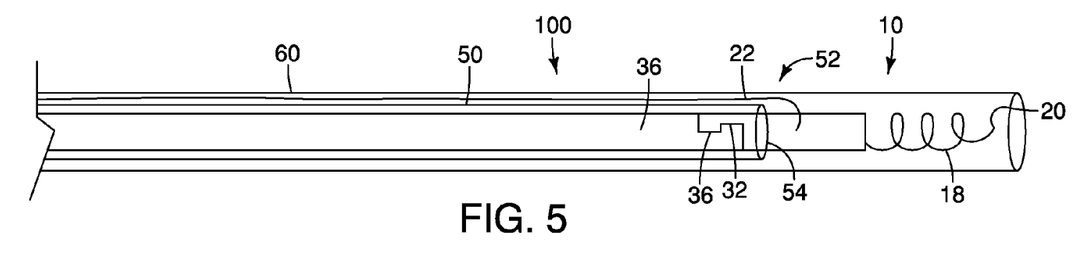
FIG. 5 is a side sectional view of an embodiment of an attachment system.

FIG. 5 illustrates an embodiment of a delivery system 100 that may be used to deliver the attachment device 10 to the tissue site. The same type of system 100 may also be used to remove the attachment device from the tissue site as discussed in more detail below. As shown, the attachment device 10 is removably joined to the stylet 36 by joining the first and second retainers 26, 32 together. An inner sheath 50 is slidably positioned so that a distal end 52 of the inner sheath 50 is positioned over and distal to the joined first and second retainers 26, 32. An inner diameter 54 of the sheath 50 is sized to fit over the first and second retainers 26, 32 and hold the first and second retainers 26, 32 in the joined position. Without the sheath 50 extending over the first and second retainers 26, 32, the first and second retainers 26, 32 are easily separable.

An outer sheath 60 is slidably positioned over the inner sheath 50 and is distally extendable so that a distal end 62 of the outer sheath 60 extends distal to the distal end 20 of the attachment device 10 as shown in FIG. 5. The outer sheath 60 may be used to deliver the attachment device 10 to a treatment site so that the distal end 20 is not exposed while the device 10 is being guided through a patient's lumen. Once the device 10 is near the tissue site having the perforation to be joined, the outer sheath 60 may be withdrawn to expose the distal end 20 of the attachment device 10.

Figure 6:
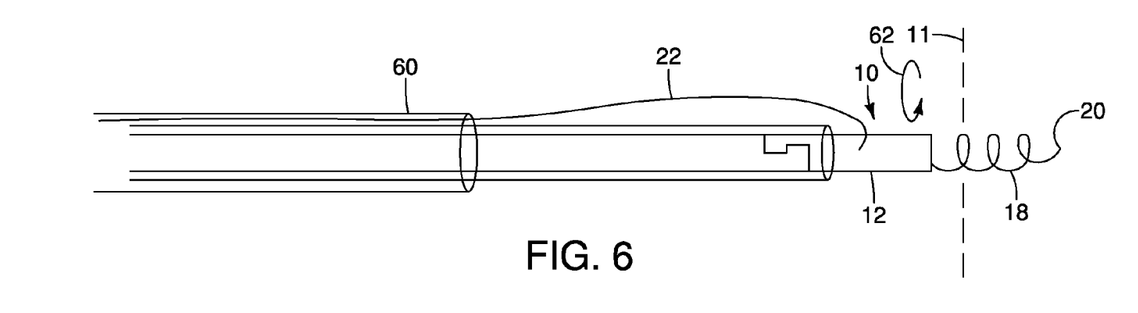
FIG. 6 is a side sectional view of the attachment system shown in FIG. 5 with the outer sheath withdrawn.
Figure 7:
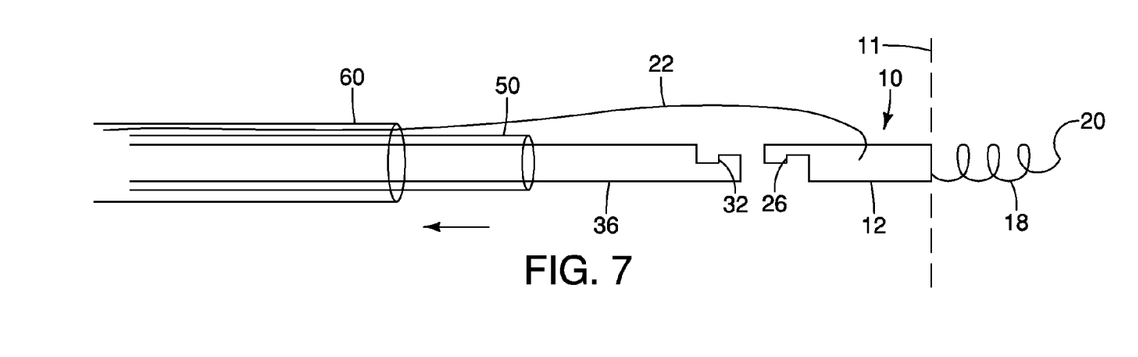
FIG. 7 is a side sectional view of the attachment system shown in FIG. 6 with the inner sheath withdrawn.

FIGS. 6 and 7 illustrate delivery of the attachment device 10 to a tissue 11. As shown in FIG. 6, the outer sheath 60 is proximally withdrawn so that the distal end 20 of the attachment device 10 is exposed. The distal end 20 may include a sharp tip to facilitate entry of the tissue attachment portion 18 into the tissue 11. With the distal end 20 positioned at the entry site, the stylet 36 may be rotated in an insertion direction 62 using a handle (not shown) so that the attachment device 10 also rotates and the tissue attachment portion 18 is rotatably inserted into the tissue 11. The inner sheath 50 is positioned over the first and second retainers 26, 32 to maintain the connection between the first and second retainers 26, 32 while the tissue attachment portion 18 is rotatably inserted so that the body 12 moves with the stylet 36. If the position of the tissue attachment portion 18 is incorrect, the stylet 36 may be rotated in the opposite direction to the insertion direction 62 to withdraw the tissue attachment portion 18 from the tissue 11. The tissue attachment portion 18 may then be reinserted in another position. The physician will know the length of the attachment portion 18 so that the depth that the attachment portion 18 is inserted into the tissue is controlled. Once the tissue attachment portion 18 is securely positioned in the tissue 11 in the desired position, the inner sheath 50 may be proximally withdrawn to release the mating connection between the first and second retainers 26, 32 as shown in FIG. 7. With the inner sheath 50 withdrawn, the attachment device 10 is released from the stylet 36. The stylet 36, the inner sheath 50 and the outer sheath 60 may be proximally withdrawn from the patient. The free end 25 of the suture 22 may extend proximally and external to the patient so that the physician may access the free end 25 to facilitate connecting the suture 22 of one attachment device 10 to the sutures 22 of one or more additional attachment devices 10 as described in detail below. In some embodiments, the suture 22 may be pulled proximally to retract the tissue into which the device 10 is inserted. The helical shape of the attachment portion 18 may be used to retract the tissue using greater force than can be used with a straight device.

Figure 8:
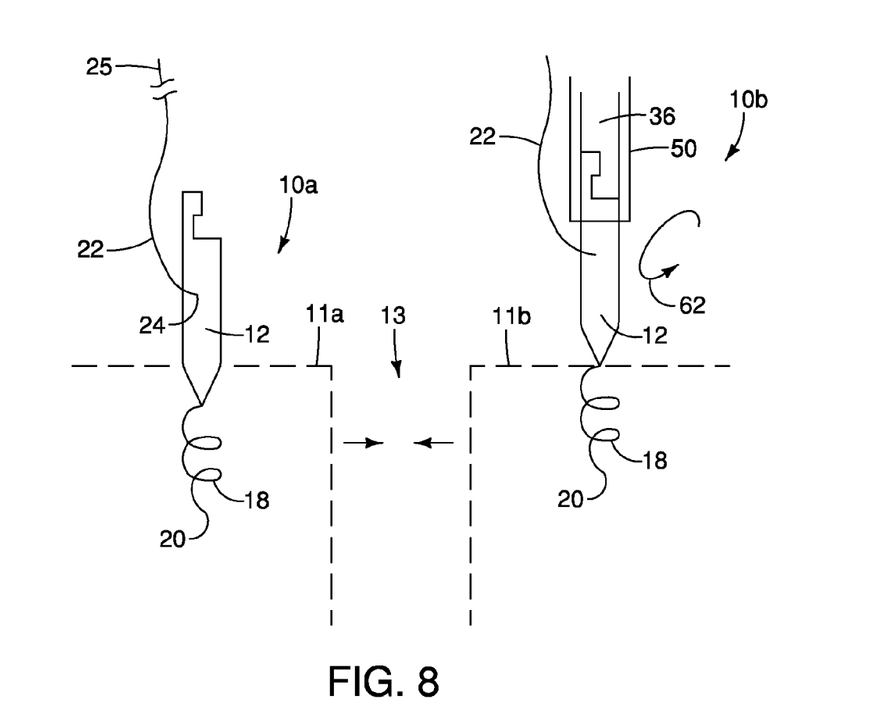
FIG. 8 illustrates insertion of an embodiment of the attachment device into a tissue.

FIG. 8 illustrates a first attachment device 10a positioned in the tissue 11a so that the tissue attachment portion 18 is implanted into the tissue 11 and at least a portion of the body 12 and the suture 22 extend above the tissue 11. A perforation 13 is shown between the tissues 11a and 11b. A second attachment device 10b is shown in FIG. 8 being positioned into the tissue 11b. The stylet 36 is being rotated in the insertion direction 62 so that the distal end 20 of the tissue attachment portion is rotatably inserted into the tissue 11b.

Figure 9:
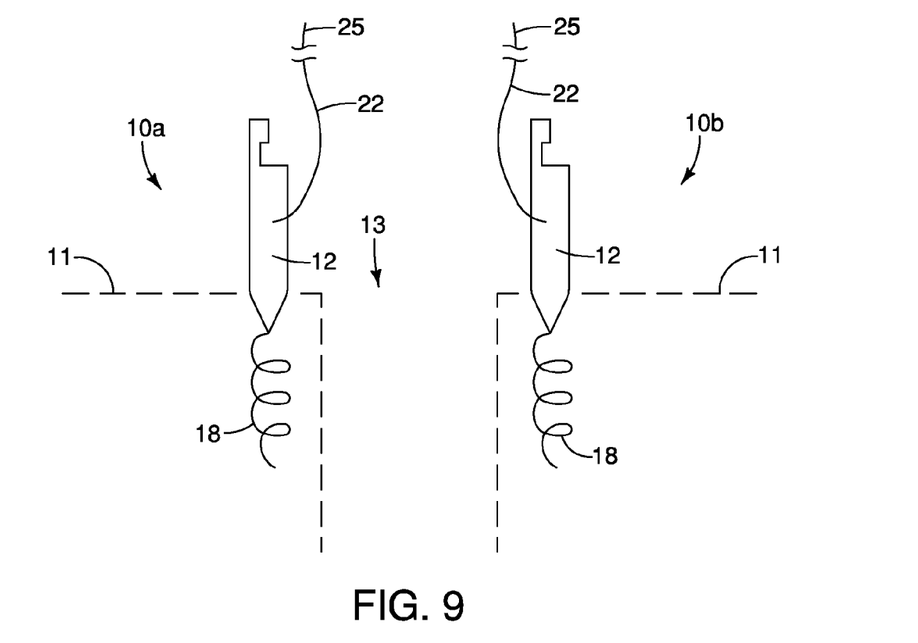
FIG. 9 insertion of an embodiment of the attachment device into a tissue.

FIG. 9 illustrates to attachment devices 10a, 10b positioned in tissue 11a, 11b on opposite sides of the perforation 13. The delivery system 100 has been withdrawn so that only the attachment devices 10a, 10b remain in the patient. The sutures 22 have free ends 25 that extend proximally so that the sutures 22 and thus the attachment devices 10a, 10b can be easily joined to approximate the tissues 11a, 11b and close the perforation 13.

Figure 10:
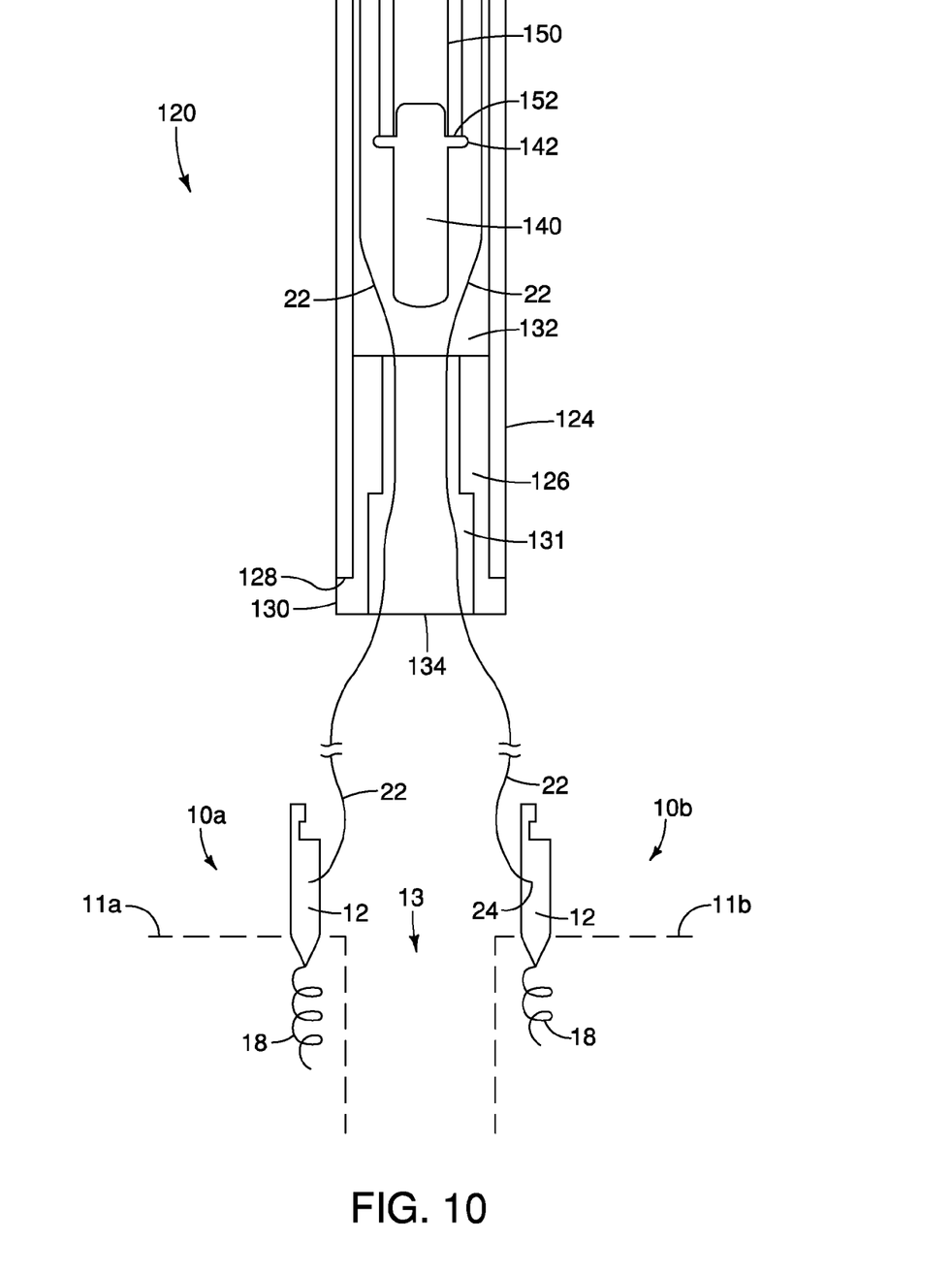
FIG. 10 illustrates an embodiment of a suture lock system and an embodiment of the attachment device.

The sutures 22 may be held together using a suture lock as described briefly herein. Exemplary suture locks may be found in U.S. Publication 2008/0300629 which is herein incorporated by reference in its entirety. FIG. 10 illustrates an embodiment of a suture lock system 120 that may be employed to join the attachment devices 10a, 10b together to approximate the tissues 11a, 11b and close the perforation 13. The suture lock system 120 includes a suture lock 121 having a sleeve 126 and a locking body 140. The suture lock system 120 includes an outer catheter 124 that includes the sleeve 126 positioned at a distal end 128 of the outer catheter 124. The sleeve 126 may include a shoulder 130 that abuts the distal end 128 so the outer catheter 126 can push the sleeve 126 into position as described below. The sleeve 126 may include a cavity 131 that is sized and shaped to accommodate a plurality of attachment devices 10. The cavity 131 may accommodate 1, 2, 3, 4 or more attachment devices 10. The outer catheter 124 includes a lumen 132 extending at least partially therethrough. The sleeve 126 is positioned at least partially within the lumen 132 and is releasable from the outer catheter 124. The sleeve 126 includes a lumen 134 extending therethrough.

The suture lock system 120 further includes the locking body 140 that is sized and shaped to at least partially fit within the lumen 134 of the sleeve 126 and to secure one or more sutures 22 extending through the lumen 134. The locking body 140 may include a shoulder 142 as shown in FIG. 10. The suture lock system 120 may also include an inner catheter 150 that is sized to coaxially extend within the lumen 132 of the outer catheter 124. The inner catheter 150 includes a distal end 152 that may abut the shoulder 142 of the locking body 140 so the inner catheter 150 may advance the locking body 140 to a locked position as described below.

Figure 11:
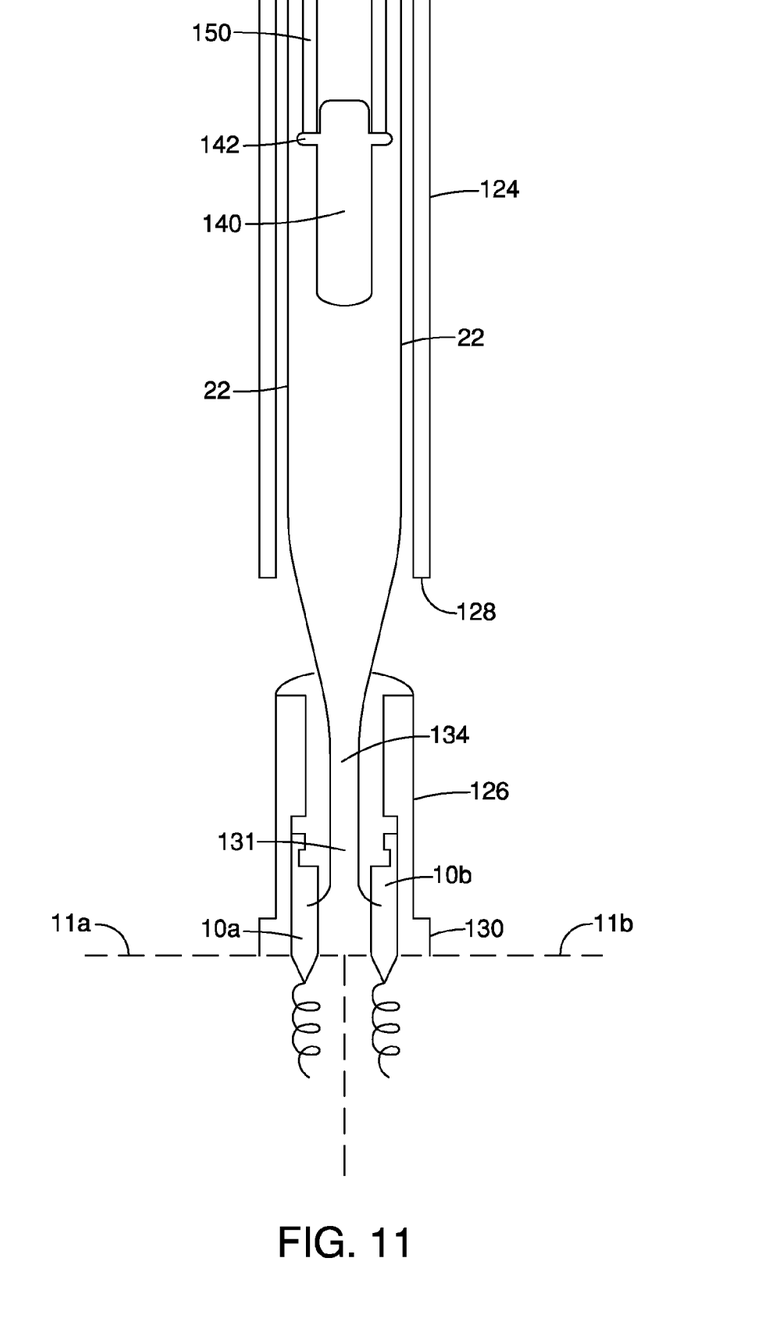
FIG. 11 illustrates an embodiment of a suture lock system and an embodiment of the attachment device.
Figure 12:
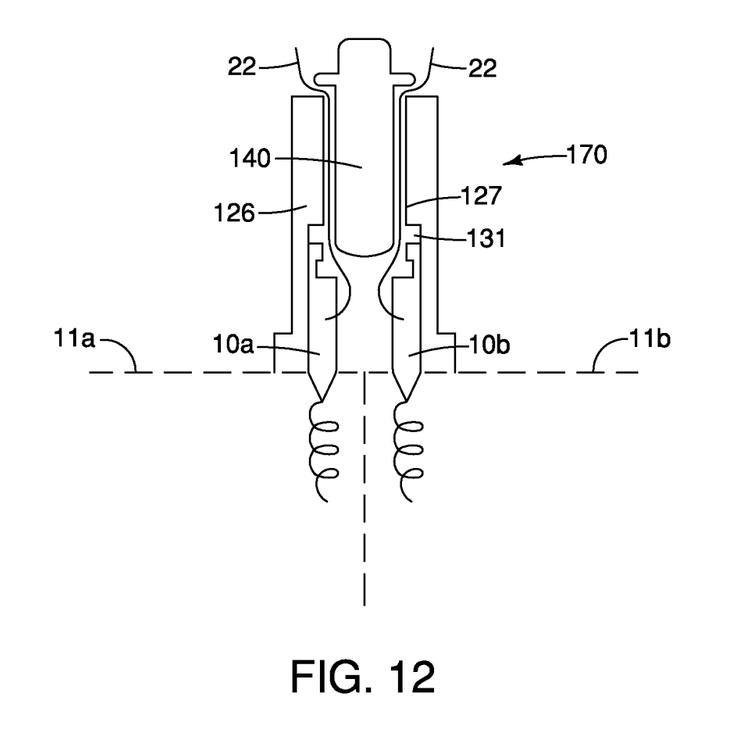
FIG. 12 illustrates an embodiment of the suture lock system secured to an embodiment of the attachment device.

FIG. 11 illustrates the tissue 11a, 11b having been approximated by pulling the sutures 22 to join the tissue 11a, 11b together to close the perforation 13. The outer catheter 124 has been proximally withdrawn and the sleeve 126 released from the outer catheter 124. The sleeve 126 is shown with the shoulder 130 positioned against the tissue 11a, 11b and with the attachment devices 10a, 10b positioned within the cavity 131 of the sleeve 126. The sutures 22 extend through the lumen 134 of the sleeve 126 and into the lumen 132 of the outer catheter 124. The inner catheter 150 is advanceable within the outer catheter 124 to move the locking body 140 to a locked configuration 170 shown in FIG. 12. In the locked configuration 170, the plurality of sutures 22 are secured between a wall 127 the sleeve 126 and the locking body 140 so that the sutures 22 may be tensioned to maintain the position of the tissue 11a, 11b. The attachment devices 10a, 10b are held within the cavity 131 of the sleeve 126 with the tissue attachment portions 18 secured within the tissue 11a, 11b and the tissue 11a, 11b approximated. The attachment devices 10a, 10b remain locked in position so that the perforation can heal. Once the perforation is healed, the attachment devices 10a, 10b, the sleeve 126 and locking body 140 will eventually slough off and pass naturally.

Figure 13:
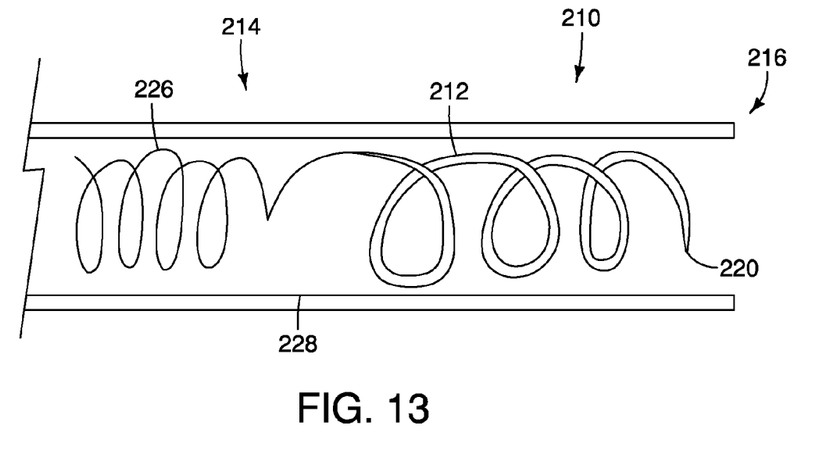
FIG. 13 is a partial side view of an embodiment of an attachment device.

FIG. 13 illustrates an embodiment of an attachment device 210 in accordance with the present invention. The attachment device 210 includes a tissue attachment portion 212 having a proximal portion 214 and a distal portion 216. In some embodiments, the tissue attachment portion 212 is a helical member having a sharp distal end 220 for piercing a patient's tissue and may be similar to the tissue attachment portion 18 described above. The attachment device 210 may be delivered to the site and rotationally inserted using a torque cable 226 operably connected to the attachment device 210. The attachment device 210 may be delivered to the site within an outer sheath 228 so that the attachment portion 212 or the distal tip 220 does not contact an accessory channel of a delivery device such as an endoscope or a patient's tissue until the attachment device 210 is at the proper position.

Figure 14A:
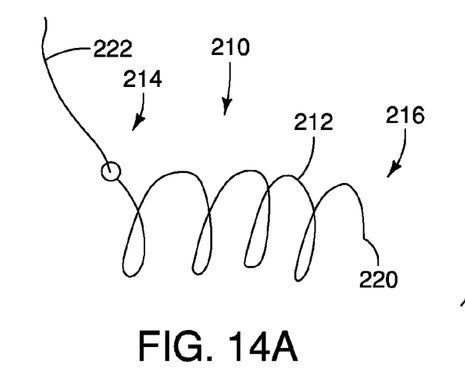
FIGS. 14A and 14B illustrate embodiments of attachment devices including a suture.
Figure 14B:
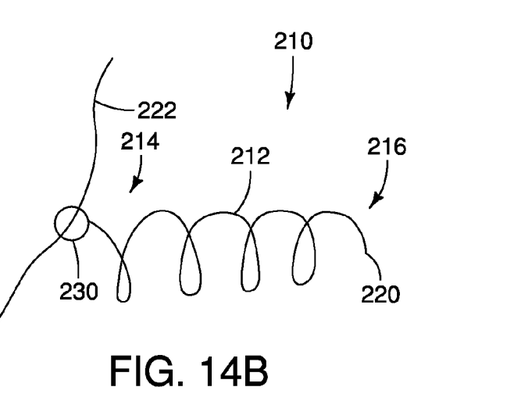

In some embodiments, the attachment device 210 further includes a suture 222 operably connected to the proximal portion 214 of the device 210 as shown in FIG. 14A. In some embodiments, the attachment device 210 may include a loop 230 at the proximal portion 214. The suture 222 may be threaded through the loop 230. Similar to the embodiments described above, the suture 222 may be used to join the device 210 to other attachment devices 210 or to retract the tissue to which the device 210 is inserted. A plurality of devices 210 may be positioned in adjacent tissue sites similar to the devices 10 described above to approximate tissue portions and may be secured using a suture lock as described above. The closure may be a purse string closure with multiple devices 210 being pulled together using the sutures 222.

The attachment devices described herein may also be removed from the tissue site using a device like the delivery system described above. By way of non-limiting example, the removal of the attachment device 10 will be described with respect to the delivery system 100 and FIGS. 5-7. If multiple attachment devices 10 are joined together by the suture 22 or other attachment, the suture 22 may be cut using a cutting device before removal of each attachment device 10. To remove the attachment device 10, the insertion method shown in FIGS. 5-7 may be reversed. The stylet 36 is extended from the inner sheath 50 and the outer sheath 60 and the first and second retainers 26, 32 are aligned as shown in FIG. 7. The stylet 36 is advanced toward the attachment device 10 so the attachment device 10 is joined to the stylet 36 and the first and second retainers 26, 32 are joined. The inner sheath 50 is advanced toward the tissue until the first and second retainers 26, 32 that are rejoined are covered by a portion of the inner sheath 50 as shown in FIG. 6. The stylet 36 may be rotated in a direction opposite the insertion direction 62 using a handle (not shown) so that the attachment device 10 also rotates and the tissue attachment portion 18 is rotatably removed from the tissue 11. The inner sheath 50 is positioned over the first and second retainers 26, 32 to maintain the connection between the first and second retainers 26, 32 while the tissue attachment portion 18 is rotatably removed so that the body 12 moves with the stylet 36. Once the tissue attachment portion 18 of the attachment device 10 is completely removed from the tissue, the outer sheath 60 may be advanced over the inner sheath 50 and the tissue attachment portion 18 to cover the distal end 20 of the attachment device 10 as shown in FIG. 5. The outer sheath 60 may be used to remove the attachment device 10 from the patient so that the distal end 20 is not exposed while the device 10 is being guided through a patient's lumen.

The materials used to form the attachment devices described herein and the suture lock may be any biocompatible materials suitable for implantation in a bodily lumen. By way of non-limiting example, the tissue attachment portion may be made from any suitable biocompatible metal, such as stainless steel and shape memory alloys, such as nitinol or plastic that are sufficiently rigid to maintain the shape the tissue attachment portion throughout the procedure. The tissue attachment portion is not intended to change shape once the portion is inserted into the tissue. The body, the sleeve and the locking body may be formed from any suitable material such as stainless steel, titanium, nitinol or other metals/alloys as well as various ceramics and plastic materials, such as polycarbonates, polyamides including nylon, polytertrafluorethylenes (i.e. PTFE and EPTFE), polyethylene ether ketones (PEEK), poly vinyl chlorides, polyimides, polyurethanes, and polyethylenes, including multi-layer or single layer constructions with or without reinforcement wires, coils or filaments. The sutures may be made from common suture material as known in the art, for example polyester suture such as 4-0 Tevdek®, nylon, silk, polypropylene, ultra high molecular weight polyethylene (UHMPE) and the like. The sutures may be monofilament, braided, twisted or multifilament.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A method of attaching a suture to a tissue for apposition or manipulation of the tissue, the method comprising:
    forming a releasable connection between a stylet having a retaining portion and an attachment device having a complementary retaining portion;
    positioning an inner catheter over the connection to hold the stylet and the attachment device together at the retaining portions;
    positioning a first tissue attachment portion of the attachment device at a first tissue site;
    rotating the stylet in an insertion direction to insert a distal tip of the tissue attachment portion into a tissue with the inner catheter positioned over the connection, the tissue attachment portion retaining its shape throughout the insertion;
    proximally withdrawing the inner catheter proximal to the connection to release the stylet from the attachment device;
    withdrawing the stylet and the attachment device remains with at least a portion of the attachment device positioned in the tissue;
    inserting a second tissue attachment portion at a second tissue site;
    approximating the first tissue site to the second tissue site to close a perforation by pulling on a first suture of the first attachment device and a second suture of a second attachment device.

2. The method of claim 1, comprising delivering a sleeve of a suture lock over the first and second sutures.

3. The method of claim 2, comprising delivering the suture lock using an inner catheter and an outer catheter.

4. The method of claim 2, comprising positioning a cavity in the sleeve over at least a portion of the first and second attachment devices.

5. The method of claim 1, further comprising removing the attachment device from the tissue.

6. The method of claim 1, further comprising positioning an outer sheath coaxially extending with the inner catheter over a distal end of the attachment device for delivery to the tissue.

7. A method of attaching a suture to a tissue for apposition or manipulation of the tissue, the method comprising:
    forming a releasable connection between a stylet having a retaining portion and an attachment device having a complementary retaining portion;
    positioning an inner catheter over the connection to hold the stylet and the attachment device together at the retaining portions;
    positioning a first tissue attachment portion of the attachment device at a first tissue site;
    rotating the stylet in an insertion direction to insert a distal tip of the tissue attachment portion into a tissue with the inner catheter positioned over the connection, the tissue attachment portion retaining its shape throughout the insertion;
    proximally withdrawing the inner catheter proximal to the connection to release the stylet from the attachment device;
    withdrawing the stylet and the attachment device remains with at least a portion of the attachment device positioned in the tissue;
    inserting a second tissue attachment portion at a second tissue site;
    inserting a second attachment device at a second tissue site by forming a second releasable connection between the stylet having the retaining portion and a second attachment device having a second complementary retaining portion;
    positioning the inner catheter over the second connection to hold the stylet and the second attachment device together at the retaining portions;
    positioning a second tissue attachment portion of the second attachment device at a second tissue site;
    rotating the stylet in an insertion direction to insert a distal tip of the second tissue attachment portion into the second tissue site;
    proximally withdrawing the inner catheter proximal to the second connection to release the stylet from the second attachment device; and
    withdrawing the stylet.

* * * * *